US006294365B1

(12) United States Patent
De Rosier et al.

(10) Patent No.: US 6,294,365 B1
(45) Date of Patent: *Sep. 25, 2001

(54) METHOD AND FORMULATION FOR STABILIZATION OF ENZYMES

(75) Inventors: Therese A. De Rosier, Milwaukee; Norberto B. de la Cruz, Wauwatosa; Richard K. Wilkosz, New Berlin, all of WI (US)

(73) Assignee: Molecular Biology Resources, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/164,060

(22) Filed: Sep. 30, 1998

Related U.S. Application Data

(63) Continuation of application No. 08/675,697, filed on Jul. 3, 1996, now Pat. No. 5,876,992.

(51) Int. Cl.$^7$ ..................................................... C12N 9/96
(52) U.S. Cl. ................................................ 435/188; 435/6
(58) Field of Search .......................................... 435/188, 6

(56) References Cited

U.S. PATENT DOCUMENTS

| | | | |
|---|---|---|---|
| 4,451,569 | 5/1984 | Kobayashi et al. | 435/188 |
| 4,891,319 | 1/1990 | Roser | 435/188 |
| 5,098,893 | 3/1992 | Franks et al. | 514/54 |
| 5,130,238 | 7/1992 | Malek et al. | 435/91 |
| 5,240,843 | 8/1993 | Gison et al. | 435/188 |
| 5,399,491 | 3/1995 | Kacian et al. | 435/91.21 |
| 5,409,818 | 4/1995 | Davey et al. | 435/91.21 |
| 5,464,614 | 11/1995 | Meyer | 424/94.3 |
| 5,556,771 | 9/1996 | Shen et al. | 435/91.2 |
| 5,580,856 | 12/1996 | Prestrelski et al. | 514/21 |
| 5,876,992 | * 3/1999 | DeRosier et al. | 435/188 |

FOREIGN PATENT DOCUMENTS

| | | |
|---|---|---|
| 0 365 685 B1 | 5/1990 | (EP) . |
| 0 415 567 A2 | 3/1991 | (EP) . |
| 0 726 310 A1 | 8/1996 | (EP) . |
| 2 009 198 A | 6/1979 | (GB) . |
| 2 126 588 A | 3/1984 | (GB) . |
| WO 89/06542 | 7/1989 | (WO) . |
| WO 89/06976 | 8/1989 | (WO) . |
| WO 93/00807 | 1/1993 | (WO) . |
| WO 93/13752 | 7/1993 | (WO) . |
| WO 94/16107 | 7/1994 | (WO) . |

OTHER PUBLICATIONS

Alonso et al., "Solvent Denaturation and Stabilization of Globular Proteins," *Biochemistry*, 30:5974–5985 (1991).

BSI Surface Modification Sciences, "Material Safety Data Sheet," BSI Corporation, Eden Prairie, MN, Jan. 94–010152.03, pp. 1–3 (Jan., 1994).

Carpenter et al., "Stabilization of Phosphofructokinase With Sugars During Freeze–Drying: Characterization of Enhanced Protection in the Presence of Divalent Cations," *Biochimica et Biophysica Acta*, 923:109–115 (1987).

Compton, J., "Nucleic Acid Sequence–Based Amplification," *Nature*, 350:91–92 (Mar. 7, 1991).

Crowe et al., "Preservation of Dry Liposomes Does Not Require Retention of Residual Water," *Proc. Natl. Acad. Sci.*, 84:1537–1540 (Mar., 1987).

Davanloo et al., "Cloning and Expression of the Gene for Bacteriophage T7 RNA Polymerase," *Proc. Natl. Acad. Sci., USA*, 81:2035–2039 (Apr., 1984).

Document No. CH 1076–01, "Material Safety Data Sheet," Ficoll 70, Pharmacia, 2 pages.

Document No. CH 1086–01, "Material Safety Data Sheet," Ficoll 400, Pharmacia, 2 pages.

Ford et al., "The Effect of Carbohydrate Additives in the Freeze–Drying of Alkaline Phosphatase," *J. Pharm. Pharmacol.*, 45:86–93 (1993).

Gianfreda et al., "Enzyme Stabilization: State of the Art," *Mol. & Cell. Biochem.*, 100:97–128 (1991).

Hillenbrand et al., "Discriminatory Function of Ribonuclease H in the Selective Initiation of Plasmid DNA Replication," *Nucleic Acids Res.*, 10(3):833–853 (1982).

Houts et al., "Reverse Transcriptase From Avian Myeloblastosis Virus," *J. Virol.*, 29(2):517–522 (Feb., 1979).

Kievits et al., "NASBA® Isothermal Enzymatic in vitro Nucleic Acid Amplification Optimized for the Diagnosis of HIV–1 Infection," *J. Virol. Methods.*, 35:273–286 (1991).

Products for Cell Culture: Cell Separation and Culture, "Culture Media Supplements: Ficoll 70 , Ficoll 400," and "Physical Separation Methods: Ficoll 400," 2 pages.

Sigma Catalog, Sigma Chemical Company, St. Louis, MO p. 284 (1993).

Tsou, C.–L., "Conformational Flexibility of Enzyme Active Sites," *Science*, 262: 380–381 (Oct. 15, 1993).

van der Vliet et al., "Nucleic Acid Sequence–Based Amplification (NASBA) for the Identification of Mycobacteria," *J. Gen. Micro.*, 139:2423–2429 (1993).

\* cited by examiner

Primary Examiner—Donna C. Wortman
(74) *Attorney, Agent, or Firm*—Marshall, O'Toole, Gerstein, Murray & Borun

(57) ABSTRACT

The present invention is directed to a method and a formulation for the stabilization of an enzyme for storage at temperatures above freezing. Specifically, the invention involves the use of formulated excipients that when added to an enzyme or mixture of enzymes and subsequently lyophilized renders stability. Upon reconstitution, the stabilized materials are useful in assays, diagnostic or molecular biology research kits, and other biological applications.

66 Claims, 2 Drawing Sheets

METHOD AND FORMULATION FOR STABILIZATION OF ENZYMES

This application is a continuation of Ser. No. 08/675,697, filed Jul. 3, 1996, now U.S. Pat. No. 5,876,992.

BACKGROUND OF THE INVENTION

A. Field of the Invention

The present invention relates to the formulation of a wet mixture of biochemicals used to enhance stability of biologically active materials, particularly enzymes, both during and after lyophilization. Removal of water from this mixture by lyophilization in the presence of stabilizing agents results in a lyophilized enzyme that is stable at room temperature over extended periods of time. This invention also relates to an improved combination of stabilizing agents useful in a process for lyophilizing an enzyme. The combination is capable of providing enhanced stability of enzymes stored at temperatures above freezing.

B. Background

Enzymes are unstable in aqueous systems at room temperature, and so are typically stored either in a frozen state, or liquid at −20° C. (−70° C. in some cases) in the presence of stabilizers such as glycerol that have low freezing points and low vapor pressures. Even under these storage conditions, repeated thawing and handling at room temperature can lead to loss of activity.

The stabilization of enzymes involves the prevention of irreversible protein denaturation which may occur for a variety of reasons including thermal denaturation and others. Unfolded or denatured proteins have altered structures, which affects the arrangement of the active site and renders them catalytically inactive (Tsou, 1993).

In an attempt to prevent loss of enzymatic activity, a number of stabilization methods have been used. Methods of stabilization may be categorized into four groups: (1) addition of excipients; (2) use of organic solvents (chemical modification); (3) immobilization (conjugation to solid/soluble phases); and (4) protein engineering techniques (Gianfreda and Scarfi, 1991). The method of stabilization described herein involves the use of soluble excipients.

Excipients are inert substances that give a desired characteristic to solvents. Examples of such excipients include sugars, glycerol, polyethylene glycols, amino acids, and other osmolytes. Certain hydrophilic excipients confer stability by making the solvent more polar. An increase in solvent polarity results in an increase in the free energy of transfer for the hydrophobic amino acid moieties from within the protein to the solvent thereby making it more difficult for the protein to unfold (Alonso and Dill, 1991). Glycerol is a common excipient used by enzymologists for storage of enzymes at low temperatures (−20° C.), since some enzymes stored frozen in 50% glycerol buffers may retain much of their initial activity for years.

Combining enzymes of interest with a stabilizing mixture may not alone be sufficient to confer shelf stability. One of the processes used to give proteins long-term stability is drying. When used in conjunction with a stabilizing formulation, drying can yield a very stable product. Methods of drying are generally of two types: (1) air drying and (2) lyophilization. Air drying involves drying under conditions of ambient or elevated temperatures at atmospheric pressure. Lyophilization is a drying process in which water molecules are removed from a frozen solution under a vacuum.

Lyophilization first requires that the aqueous solution be frozen and preferably quick-frozen. One means of quick-freezing a solution is immersing it into liquid nitrogen. A high vacuum is then applied to the frozen sample, which results in sublimation, or vaporization of ice phase at subzero temperatures (primary drying). Residual moisture can be subsequently removed by allowing the temperature to gradually rise (secondary drying) (FTS Systems, Inc., Bulletin #1). The resulting freeze-dried product is a dry, crystalline substance or a powder. Substances that are lyophilized are often hygroscopic, that is, they will tend to absorb atmospheric moisture and lose their stability. In the presence of certain additives, however, it is possible to produce material that is not hygroscopic.

Stabilization and storage of materials using carbohydrates as cryoprotectants has been described by Franks and Hatley (U.S. Pat. No. 5,098,893), but the drying process uses conditions of ambient or elevated temperatures near atmospheric pressure. Use of sugars causes a glassy matrix or rubbery state to form, which when anhydrous, stabilizes the material of interest. Roser, in U.S. Pat. No. 4,891,319 and European Patents WO 87/00196, WO 89/06542, WO 89/06976, EP 0 415 567 A2, describes the process of stabilizing biological materials such as proteins, viruses, and other macromolecules by drying under ambient conditions and at atmospheric pressure in the presence of the carbohydrate trehalose.

The use of sugars such as the disaccharide trehalose as stabilizing agents has been used in conjunction with lyophilization to stabilize polysaccharides (Guthöhrlein and Helting, European Patent No. GB 2 009 198 A) and liposomes (Crowe et al., 1987). Lyophilization has also been used to stabilize tumor necrosis factor in the presence of a nonionic surfactant and sugars such as trehalose (Hayashi and Komiya, European Patent No. GB 2 126 588 A). Enzymes that have been stabilized with sugars during lyophilization include phosphofructokinase (Carpenter et al., 1987), which was stabilized with glucose, galactose, maltose, sucrose, and trehalose, and alkaline phosphatase (Ford and Dawson, 1992) which was stabilized with mannitol, lactose, and trehalose.

There is still a need in the art for new and better methods of formulations that stabilize enzymes, particularly enzymes for use in molecular biological applications. The limited availability of freezers and refrigeration in many countries has also created a need to bring enzymes that are stable at ambient temperatures to the user. Thus, it is an object of this invention to provide stabilized enzymes that could be shipped at ambient temperatures and stored for months or years at elevated (or refrigerated [2–8° C.] or ambient) temperatures and still retain all or most of their initial activity levels. It is a further object of this invention to provide certain stabilized enzyme formulations that could be used in various test procedures that are a part of diagnostic kits and other molecular biology research kits. In accordance with these objects, the present invention provides stabilized enzymes which can be stored at temperatures above freezing, and reactivated directly before use.

Therefore, the present invention is directed to providing a formulation that when used with an enzyme or combination of enzymes will not adversely affect enzyme activity prior to and during lyophilization or after reconstitution of the enzyme. The invention is further directed to providing a formulation that when combined with an enzyme or combination of enzymes will not adversely affect enzyme activity prior to and during lyophilization or after reconstitution of the enzyme. This invention is further directed to providing a formulation that when combined with an enzyme or a combination of enzymes will confer greater stability after lyophilization than has heretofore been possible. Yet another aim is to provide a lyophilized enzyme mixture that can be applied to a diagnostic or molecular biology research test.

SUMMARY OF THE INVENTION

The present invention relates to a formulation of excipients for the stabilization of proteins (stabilizing formulation), the proteins including but not limited to enzymes or enzymatically active fragments of enzymes. The formulation comprises a carrier protein, one or more sugars, one or more disaccharides, one or more disaccharide derivatives, optionally one or more sugar polymers and/or branched sugar polymers. The formulation may either be aqueous or substantially free of water (dried formulation). The dried formulation may be reconstituted to the aqueous phase before use.

A preferred formulation comprises the sugars trehalose and maltitol, the sugar polymer dextran, along with a carrier protein, preferably an albumin, more preferably, bovine serum albumin (BSA) in a buffer solution. Neither the BSA nor sugars alone confer the thermal stability required for long-term storage. The formulation does not interfere with the individual activities of enzymes of interest, nor does it interfere with a functional multi-enzyme process that utilizes these enzymes.

Upon reconstitution in an aqueous solution, the mixture retains both individual enzyme activity and multi-functional activity. The invention provides methods for using the stabilized materials in biological applications, such as in the manufacture of diagnostic or molecular biology research kits and other applications or processes that would be apparent to those skilled in the art.

More particularly, the present invention is directed to improved methods for stabilizing enzymes or other biological materials for storage above freezing temperature, the method comprising combining the enzymes or biological materials with a stabilizing formulation (either in a lyophilized or aqueous state), the formulation comprising a carrier protein, one or more sugars, one or more disaccharides, one or more disaccharide derivatives, optionally one or more sugar polymers, and a buffer, followed by freezing and lyophilization of the frozen mixture.

Carrier proteins useful in the present invention include but are not limited to albumin (e.g., bovine serum albumin) and gelatin.

Exemplary disaccharides useful in the present invention include but are not limited to trehalose, sucrose, and others. Exemplary disaccharide derivatives useful in the present invention include maltitol, mannitol, branched sucrose polymers, for example Ficoll®, sorbitol, and others, particularly disaccharide alcohols. Exemplary sugar polymers useful in the present invention include dextran.

Buffers useful in the present invention include Tris buffers, phosphate buffers, HEPES buffers and combinations thereof.

A preferred embodiment of the present invention is directed to methods for stabilizing an enzyme or an enzymatically active fragment thereof for ambient temperature storage in the dry phase above freezing temperature. The method is comprised of combining an enzyme or an enzymatically active fragment thereof with a stabilizing formulation comprising in combination a carrier protein (typically about 1 mg/ml to about 15 mg/ml), from about 3% w/v to about 15% w/v of one or more disaccharides, from about 0% to about 10% w/v of one or more disaccharide derivatives, from about 0% to about 10% w/v of a simple sugar polymer and a compatible buffer; freezing the mixture, and lyophilizing the frozen mixture until substantially water-free. The preferred carrier protein of the method is bovine serum albumin. The preferred concentration of bovine serum albumin in the stabilizing mixture is about 3 mg/ml.

The disaccharide and disaccharide derivatives of the method are preferably selected from the group consisting of trehalose, sucrose, maltitol, mannitol, corn syrup solids, sorbitol, and branched polymers of sucrose, for example Ficoll™. A preferred disaccharide for use in the method of the present invention is trehalose. Preferably, trehalose is present at from about 6% to about 10% w/v. A preferred disaccharide derivative for use in the method of the present invention is maltitol. Preferably maltitol is present at from about 3% to about 10% w/v. A preferred simple sugar polymer for use in the method of the present invention is dextran which is present preferably at from about 2.0% to about 10% w/v. A preferred dextran is Dextran T-500. A preferred buffer for practice of the present invention consists essentially of 2.92 mM potassium phosphate, pH 7.2, 4.14 mM potassium phosphate, pH 7.5, 1.28 mM Tris-HCl, pH 7.5, 20.7 mM NaCl, 19.2 mM KCl, 0.51 mM dithiothreitol, 0.66 mM EDTA, 1.28 mM Mg-Acetate, and 0.03% Triton X-100® (a non-ionic surfactant). Enzymes stabilized by the method of the present invention may be selected from the group consisting of T7 RNA Polymerase, AMV-Reverse Transcriptase, RNase H, other enzymes known to be unstable at ambient temperature, and combinations thereof.

Further contemplated by the present invention is a stabilized mixture of enzymes or enzymatically active fragments thereof, the stabilized mixture produced by the methods of the present invention.

The invention is also directed to formulations useful for the stabilization of enzymes and other biological material, including but not limited to proteins, the formulations comprising a carrier protein, one or more sugars, and one or more disaccharides or disaccharide derivatives.

Another aspect of the present invention is directed to a mixture for use in producing a substantially water-free and stabilized formulation of one or more enzymes, or enzymatically active fragments thereof said mixture when brought to a predetermined volume by the addition of an aqueous phase comprises: a carrier protein; from about 3% to about 15% (w/v) of one or more disaccharides; from about 1% to about 10% (w/v) of one or more disaccharide derivatives; from about 0% to about 10% (w/v) of a sugar polymer; and a compatible buffer.

A preferred aqueous formulation useful for stabilizing one or more enzymes or enzymatically active fragments thereof for storage in the dry phase above freezing temperature, comprises in combination, a carrier protein (about 1 mg/ml to about 15 mg/ml), from about 3% w/v to about 15% w/v of one or more disaccharides, from about 1% to about 10% w/v of one or more disaccharide derivatives, from about 0% to about 10% w/v of a simple sugar polymer and a compatible buffer and optionally a branched polymer of sucrose. A preferred carrier protein of the improved formulation is bovine serum albumin, and its preferred concentration is about 3 mg/ml. The disaccharide and disaccharide derivatives of the formulation are preferably selected from the group consisting of trehalose, sucrose, maltitol, mannitol, corn syrup solids, sorbitol, and branched sucrose polymers, for example Ficoll™. A preferred disaccharide for use in the formulation of the present invention is trehalose. Preferably trehalose is present at from about 6% to about 10% w/v. A preferred disaccharide derivative for use in the formulation of the present invention is maltitol. Preferably maltitol is present at from about 3% to about 10% w/v. A preferred simple sugar polymer for use in the formulation of the present invention is dextran which is preferably present at from about 2.0% to about 10% w/v. A preferred buffer for practice of the present invention consists essentially of 2.92 mM potassium phosphate, pH 7.2, 4.14 mM potassium phosphate, pH 7.5, 1.28 mM Tris-HCl, pH 7.5, 20.7 mM NaCl, 19.2 mM KCl, 0.51 mM dithiothreitol, 0.66 mM EDTA, 1.28 mM Mg-Acetate, and 0.03% Triton X-100®. Enzymes stabilized by the practice of the present invention may be selected from the group consisting of T7 RNA Polymerase, AMV-Reverse Transcriptase, RNase H, other enzymes known to be unstable at ambient temperature, and combinations thereof.

The invention is also directed to aqueous formulations for stabilizing biological materials and particularly enzymes or enzymatically active fragments thereof, the formulations produced by combining a carrier protein (about 1 mg/ml to about 15 mg/ml), from about 3% w/v to about 15% w/v of one or more disaccharides, from about 1% to about 10% w/v of one or more disaccharide derivatives, from about 0% to about 10% w/v of a simple sugar polymer and a compatible buffer and optionally a branched polymer of sucrose. A preferred carrier protein of the formulation is bovine serum albumin, and its preferred concentration is about 3 mg/ml. The disaccharide and disaccharide derivatives of the formulation are preferably selected from the group consisting of trehalose, sucrose, maltitol, mannitol, corn syrup solids, sorbitol, and branched sucrose polymers, for example Ficoll™. A preferred disaccharide for use in the formulation of the present invention is trehalose. Preferably trehalose is present at from about 6% to about 10% w/v. A preferred disaccharide derivative for use in the formulation of the present invention is maltitol. Preferably maltitol is present at from about 3% to about 10% w/v. A preferred simple sugar polymer for use in the formulation of the present invention is dextran which is preferably present at from about 2.0% to about 10% w/v. A preferred buffer for practice of the present invention consists essentially of 2.92 mM potassium phosphate, pH 7.2, 4.14 mM potassium phosphate, pH 7.5, 1.28 mM Tris-HCl, pH 7.5, 20.7 mM NaCl, 19.2 mM KCl, 0.51 mM dithiothreitol, 0.66 mM EDTA, 1.28 mM Mg-Acetate, and 0.03% Triton X-100®.

The aqueous formulations of the present invention may be frozen and lyophilized to provide a substantially water free (dried) formulation which, when reconstituted to the aqueous phase, may be mixed with enzymes or enzymatically active fragments thereof, the mixture frozen and lyophilized to provide a stabilized mixture of enzymes or enzymatically active fragments thereof.

Also contemplated by the present invention are stabilized mixtures of biological materials, preferably enzymes or enzymatically active fragments of enzymes prepared according to the methods of the present invention, as well as both aqueous and substantially water free stabilizing formulations.

DETAILED DESCRIPTION OF THE INVENTION

Figure 1:
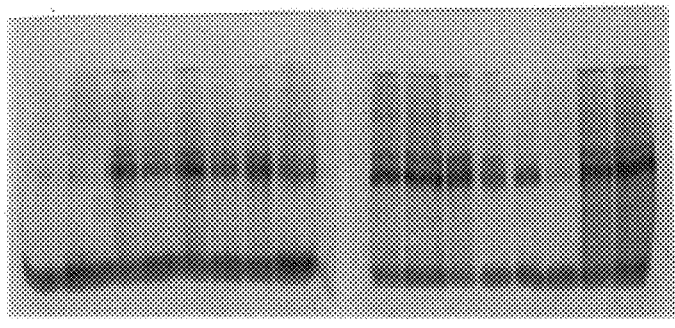
FIG. 1 is a photograph of Enzyme Linked Gel Assay (ELGA) gels, depicting the recovered NASBA® activity (undiluted and diluted product) of a three-enzyme mixture lyophilized with BSA and various sugar additives and buffers.

The following describes aqueous and dried stabilizing formulations useful for stabilizing biological materials and methods for preparing the formulations. Also described are methods for stabilizing biological materials using the formulations of the present invention. Additionally, methods and kits that involve the use of the stabilized mixture are described. Thus, as the discussion details below, the present invention has several aspects.

The following methods were used throughout the study.

I. Preparation of the Enzymes for Lyophilization

The purified enzymes that were used to study potential stabilizing excipients were T7 RNA Polymerase, Avian Myeloblastosis Virus-Reverse Transcriptase (AMV-RT) and RNase H (Molecular Biology Resources, Milwaukee, Wis.). These enzymes were stored in 50% glycerol storage buffers at −20° C. or −70° C., since glycerol lowers the freezing point of proteins closer to the storage temperature. Before lyophilization, it was necessary to remove glycerol because it acts as a hygroscopic agent and the enzyme preparations would not lyophilize. Each enzyme was individually deglycerolized by ultrafiltration into its appropriate storage buffer containing no glycerol as described below.

Deglycerolization was tested on a small scale by a buffer exchange method using Centricon® concentrators (Amicon Inc., Beverly, Mass.). The molecular weights of T7 RNA Polymerase and AMV-Reverse Transcriptase (AMV-RT) are approximately 107,000 and 160,000, respectively. Therefore a Centricon® 30 (molecular weight cut-off of 30,000) was required for buffer exchange of these enzymes. The molecular weight of RNase H is 17,600 kD, therefore a Centricon® 10 (molecular weight cut-off of 10,000) was required for buffer exchange of this enzyme.

Centricon® concentrators were pretreated with bovine serum albumin (BSA) to reduce non-specific binding (Amicon Co. Technical Note). This was done by adding BSA at 1 mg/mL in sterile water (1000μL) to each concentrator and centrifuging at 5000×g in an SA-600 fixed-angle rotor (Sorvall®, DuPont Co., Wilmington, Del.) with rubber adapters. Each sample reservoir was covered with parafilm during concentration to minimize contamination. BSA does not have a significant effect upon T7 RNA Polymerase or RNase H activity recovery. However, AMV-RT activity is sensitive to BSA from some sources upon deglycerolization. A preferred BSA preparation for AMV-RT deglycerolization is acetylated BSA (Molecular Biology Resources, Milwaukee, Wis.).

To each concentrator was added 1000 μL of the appropriate non-glycerol-containing sterile-filtered storage buffer and the concentrators were centrifuged until dead volume was reached (25–50 µl). The buffer used to deglycerolize T7 RNA Polymerase was 20 mM potassium phosphate pH 7.5, 100 mM NaCl, 1 mM dithiothreitol, 1 mM EDTA, and 100 µg/ml BSA. The buffer used to deglycerolize AMV-RT was 20 mM Tris-HCl pH 8.3, 2 mM dithiothreitol, and 40 mM KCl. The buffer for AMV-RT was different from its standard storage buffer (200 mM potassium phosphate pH 7.2, 2 mM dithiothreitol, and 0.2% (v/v) Triton X-100). A Tris-based buffer was used in subsequent drying, since use of the phosphate buffer was not optimal for activity recovery. Deglycerolization of RNase H was achieved using a buffer consisting of 20 mM Tris-HCl pH 7.5, 300 mM KCl, 0.1 mM dithiothreitol, 20 mM Mg-Acetate, 7 mM EDTA, and 200 µg/ml BSA.

To deglycerolize the enzymes, an appropriate volume of enzyme (in glycerol) was added to each concentrator. The amount that was deglycerolized was determined by the number of units required in the final lyophilization. Generally, an amount from 50–150 µL enzyme in glycerol buffer was added to the prepared concentrators. The appropriate buffer without glycerol was added to obtain a volume of about 10 times the initial enzyme volume (up to 1.5 ml total) and the two phases were thoroughly mixed by pipetting, being careful not to disrupt the filter. It is important to avoid overdilution of the enzymes with the non-glycerol buffer, since this may contribute to activity loss. Each concentrator was centrifuged in an SA-600 rotor at 5000×g for approximately 45 minutes. The process was repeated twice.

The deglycerolized enzymes were recovered by attaching the filtration unit into a retentate cup and spinning the assembly in an SA-600 rotor at 1000×g for two minutes. The filtrate from each spin was discarded. The final volume of retentate was determined by pipetting. Careful measurements of the activity of the each individual deglycerolized enzyme preparations were made to determine recovery.

The individual enzyme activity assays were performed according to standard procedures. T7 RNA Polymerase was assayed, using a modification of a protocol described by Davanloo et al. (1984). Reaction mixtures (50 µL) contained 40 mM Tris-HCl, pH 7.9 (23 ° C.), 8 mM MgCl$_2$, 5 mM DTT, 4 mM spermidine-(HCl)$_3$, 0.4 mM each CTP, GTP, ATP, pH 7.0, 0.4 mM [α$^{33}$P]UTP, pH 7.0, 25 µCi/ml, 2.5 µg T7 DNA, and 5 µl of diluted enzyme. For control purposes, well characterized stocks of T7 RNA Polymerase were simultaneously assayed in the range of 2 to 20 units/reaction. Two reactions were run without enzyme as negative controls.

The reaction was started by the addition of 5 µl of enzyme to 45 µl of the reaction mixture. After 10 minutes of incubation at 37° C., the reaction was terminated by adding 50 µl of yeast RNA co-precipitant (10 mg/ml in 0.1 M sodium acetate, pH 5.0), followed by adding one ml of 10% trichloracetic acid (TCA). The samples were then placed on ice for at least 10 minutes to allow precipitation. The mixture was then filtered on a glass fiber filter disc and washed with 5% TCA/2% sodium pyrophosphate and then with cold 100% reagent grade ethanol (Mallinkrodt, Paris, Ky.). After thorough drying, the discs were placed in vials with 5 ml of scintillation fluid and counted by a scintillation counter to determine acid-precipitable counts. One unit of activity is defined as the amount of enzyme required to incorporate 1 nmol of UTP into acid-insoluble form in 60 minutes at 37° C.

The AMV-Reverse Transcriptase assay was a variation of a protocol described by Houts, et al. (1979), the disclosure of which is incorporated herein by reference. Reactions (50 µl) contained 50 mM Tris-HCl, pH 8.3 (23° C.), 6 mM MgCl$_2$, 40 mM KCl, 1 mM DTT, 0.2 mM Poly A·(dT)$_{12-18}$(20:1), 0.5 mM [$^3$H]TTP, pH 7.0, 10 µCi/ml, and 5 µl of diluted enzyme. For control purposes, well characterized standard stocks of AMV-RT were simultaneously assayed in the range of 0.1 to 1 units/reaction. Two reactions were run without enzyme as negative controls.

A 45 µl reaction mixture, less enzyme, was pre-incubated and the reaction started by the addition of 5 µl of AMV-Reverse Transcriptase. After 10 minutes of incubation at 37° C. the reaction was terminated by spotting 40 µl onto a glass fiber filter square (1×1 cm). The square was dropped into a beaker of cold 10% trichloracetic acid (TCA)/2% sodium pyrophosphate, and swirled for at least 10 minutes. The squares were washed twice for 5 minutes each with 5% TCA/2% sodium pyrophosphate by swirling on ice. A final wash for one minute with cold 100% reagent grade ethanol (Mallinkrodt) was followed by thorough drying of the filter squares under a heat lamp. The dried filters were counted in 5 ml of scintillation fluid after soaking a minimum of 2 hours. One unit of activity is defined as the amount of enzyme required to incorporate 1 nmol of total dTTP into acid-insoluble form in 10 minutes at 37° C.

The RNase H assay follows the protocol described in Hillenbrand and Staudenbauer (1982), the disclosure of which is incorporated herein by reference. Reactions (25 µl) contained 20 mM HEPES-KOH, pH 8.0 (23° C.), 10 mM MgCl$_2$, 50 mM KCl, 1 mM DTT, 0.24 mM [α$^{-}$P]poly(A) ·poly(dT) (1:2), pH 7.0, 15 µCi/ml, and 4 µl of diluted enzyme. For control purposes, well characterized standard stocks of RNase H were simultaneously assayed in the range of 0.05 to 0.5 units/reaction. Two reactions were run without enzyme as negative controls.

A 25 µl reaction mixture, less enzyme, was prepared and the reaction started by the addition of 4 µl of RNase H. After 20 minutes of incubation at 37° C., the reaction was terminated by adding 25 µl of cold yeast RNA co-precipitant (10 mg/ml in 0.1 M sodium acetate, pH 5.0) followed by 200 µl of 10% trichloracetic acid (TCA). The samples were placed on ice for at least 10 minutes. The mixture was centrifuged for 7 minutes at 16,000×g in an Eppendorf microcentrifuge (Brinkmann Instruments, Westburg, N.Y.), and 200 µl of the supernatant fluid was withdrawn and counted in 5 ml of scintillation fluid. One unit of activity is defined as the amount of enzyme required to produce 1 nmol of acid-soluble ribonucleotide from [α$^{32}$P]poly(A)·poly(dT) in 20 minutes at 37° C.

II. Testing of Deglycerolized Enzymes in NASBA®

Once the activities of the deglycerolized enzymes were determined, samples were tested for their functional performance in an amplification procedure prior to lyophilization. The procedure NASBA®, or Nucleic Acid Sequence Based Amplification (as disclosed in Compton, 1991; Kievits, 1991; Malek, U.S. Pat. Nos. 5,130,238 and 5,409,818; each of which is incorporated herein by reference), isothermally amplifies a targeted nucleic acid sequence with a mixture of T7 RNA Polymerase, AMV-RT, and RNase H. NASBA® is a trademark of Organon Teknika (Boxtel, The Netherlands).

One of the diagnostic tests of interest employing NASBA® technology selectively amplifies ribonucleic acid for early in vitro detection of viral HIV-1 RNA with the target sequence (Kievits et al., 1991). The reactions were performed as described in Kievits et al., with minor modifications. Target, nucleotides, primers, and enzymes were mixed to allow amplification of $10^3$ and $10^2$ molecules of HIV-1 RNA per reaction. The NASBA® reaction (25 µl or an amended 20µl format) contained 40 mM Tris-HCl pH 8.5, 12 mM $MgCl_2$, 30 mM KCl, 5 mM DTT, 15% dimethlysulfoxide (DMSO), 1 mM each of dATP, dGTP, dCTP, dTTP, 0.5 mM rITP, 1.5 mM rGTP, and 2 mM rATP, rCTP, and rUTP. Forward primer (5'AGT GGG GGG ACA TCA AGC AGC CAT GCAAA 3'[SEQ ID NO: 1]) and reverse primer (5'AAT TCT AAT ACG ACT CAC TAT AGG GTG CTA TGT CAC TTC CCC TTG GTT CTC TCA 3' SEQ ID NO: 2]) were added in the final concentration of 0.2 µM per reaction. The reaction was started with the addition of 2 µl (25 µl format) or 5 µl (20 µl format) of enzyme mix, consisting of 2 units of AMV-RT, 180 units of T7 RNA Polymerase, and 0.6 units of RNase H. The reaction mixture was then incubated at 41° C. for 1.5 hours, and stopped by placing the tubes on ice.

The reaction product was detected qualitatively by the non-isotopic Enzyme-Linked Gel Assay (ELGA) (van der Vliet, 1993 which disclosure is incorporated herein by reference). In this procedure, reaction products are hybridized to a horseradish peroxidase-linked oligonucleotide probe, run on a 12.5% homogeneous native polyacrylamide gel using the Pharmacia Phast-System (Pharmacia Biotech, Inc., Piscataway, N.J.) and detected with the horseradish peroxidase substrate, tetra-methyl benzidine. Samples that contain the RNA product could be quickly determined, since bands of the hybridized RNA-probe run distinctively slower than free oligonucleotide-probe. Dilutions of the product run on a gel allow for further qualification.

III. Testing of Additives for Stabilization of Enzyme Activity

In the search for stabilizers to use with enzymes, a number of chemicals were tested. An initial screening of excipients was done to test for additives that would not interfere with the activity of individual enzymes, nor with their use in the NASBA® reaction.

A survey of additives was made by adding individual sugars (5–30% final concentration) to individual enzymes or a mixture of enzymes. A stabilizing mixture was also tested for use with a lyophilized enzyme mixture. This formulation comprises a solution of bovine serum albumin, maltitol, trehalose, dextran, and Universal buffer.

IV. Lyophilization of the Enzymes

To prepare enzymes for lyophilization, a homogeneous pre-mixture of the stabilizing additives was made. The individual deglycerolized enzymes (see Section I) were then added in the proper ratio of activities for use in NASBA®, with gentle mixing. A "Universal Buffer" (2.92 mM potassium phosphate pH 7.2, 4.14 mM potassium phosphate pH 7.5, 1.28 mM Tris-HCl pH 7.5, 20.7 mM NaCl, 19.2 mM KCl, 0.51 mM dithiothreitol, 0.66 mM EDTA, 1.28 mM Mg-Acetate, and 0.03% Triton X-100) was prepared to approximate the ionic and salt conditions present in a wet solution that worked well in NASBA®. This buffer was added to the lyophilization mixture to bring the volume to an appropriate level for easy manipulation.

The first step in lyophilization is a quick-freeze of the sample in liquid nitrogen by one of two methods. The first method of freezing involved pipetting aliquots of the formulation into plastic test tubes, and then immersing the tubes into a container of liquid nitrogen for 5 minutes. Once the samples were frozen, tubes were removed from the liquid nitrogen and placed into chilled blocks that accommodate the tubes and were set on dry ice. The blocks were then placed into a pre-cooled vacuum vessel, and the closed vessel was set on a bed of dry ice.

The other freezing method involved the formation of frozen spheres. Spheres of the formulation were created by dropping aliquots from a pipettor directly into liquid nitrogen and allowing them to freeze for 5 minutes. The spheres were then placed directly onto a pre-cooled tray which was then inserted into the vessel, closed, and set on a bed of dry ice.

Vacuum was applied to the vessel in the 20–50 millitorr range, and lyophilization was allowed to proceed for 24 hours. The primary phase was allowed to occur overnight, and then a secondary sublimation occurred by removing the flask from dry ice and allowing further drying for 2–4 hours at room temperature. The samples were harvested by releasing the vacuum to the flask, followed by backfilling with nitrogen gas. Tubes containing lyophilized samples were removed from the chamber and capped. The tray containing dried spheres was removed and spheres were placed into individual tubes. Samples were stored desiccated at the appropriate temperature.

Ideally, the samples appear as a dry white powder. The residual water in the freeze-dried samples was analyzed using the Karl Fischer coulometric technique, which measures moisture content by a complex redox titration. Typically, the drying process in the absence of glycerol removed greater than 97% of the initial water.

V. Testing for Recovery of Enzyme Activities

Lyophilized samples (see Section IV above) were reconstituted either by the addition of 50% glycerol or sterile water. An initial test for recovery of each individual enzyme activity was performed according to the assay procedures described in Section I above. Recovery of activity was also tested in the NASBA® reaction (see Section II above). Percent recovery of activity was determined against a standard wet formulation stored at −20° C.

Once it was established that each individually lyophilized enzyme preparation (i.e., T7 RNA Polymerase, AMV-RT and RNase H) had recovered activity, then T7 RNA Polymerase, AMV-RT, and RNase H were combined and lyophilized as an enzyme mixture in the presence of various additives. The reconstituted enzyme mixture was tested for each individual enzyme activity, as well as in NASBA®.

VI. Stability Study on Lyophilized Enzymes

Stability studies were performed in two phases: 1) a quick evaluation of additives to the mixture to be lyophilized, and 2) full-scale accelerated degradation work on combinations of additives that showed promise based on observations made in the first phase.

To simulate the effect of a long-term, low temperature storage, samples of lyophilized enzyme mixture were exposed to storage temperatures from −20° C. to 65° C. for short periods of time.

The lyophilized samples were reconstituted either by the addition of 50% glycerol or sterile water before immediate use. Reconstituted samples were stored at 4° C. and then tested for both recovery of individual activity and their ability to function in the NASBA® reaction.

Stability studies were initially performed on each individual enzyme. Once it was determined that each enzyme could be stabilized by lyophilization with the formulated additives, then the enzyme was substituted for a wet enzyme in the three-enzyme mixture. Substitution of reconstituted dried for wet enzyme was performed first with one enzyme at a time, then two at a time, and finally with all three dried enzymes. Although each individual enzyme in the dried three-enzyme mix was assayed for activity, it was the ability to function in the NASBA® reaction that was the definitive test for retained activity.

Examples 1 to 4 illustrate the process in which a solution containing these enzymes was incorporated into a formulation of stabilizers and subsequently made stable through lyophilization. As a first step in the study of shelf-stability of the three enzymes of interest, Example 1 shows the ability to formulate a freeze-dried mixture of enzymes and stabilizers from which we were able to recover NASBA® activity upon reconstitution, as checked against a wet enzyme mixture.

Example 2 illustrates the ability of the stabilizing mixture to confer recovered activity on the lyophilized enzyme mixture upon reconstitution.

Example 3 is a short-term stability study set up on a freeze-dried enzyme mix at temperatures of −20° C., 4° C., 22° C., 37° C., 50° C., and 65° C. for 1 week.

Example 4 details a long-term stability study set up with lyophilized enzyme mix at storage temperatures of −20° C., 4° C., 22° C., 37° C., and 50° C. for 3 months.

EXAMPLE 1

Preparation of Stabilizing Formulations

Studies were conducted to find improved stabilizing formulations (and methods for stabilizing) which extend the shelf life of enzymes or biological products at temperatures above freezing.

Lyophilization experiments of the individual enzymes in combination with BSA and sugar additives were performed as described above. The various reducing and non-reducing sugars tested were trehalose, sucrose, maltitol, mannitol, sorbitol, corn syrup solids, and Ficoll®, a branched polymer of sucrose (Pharmacia Biotech Inc., Piscataway, N.J.). Buffers tested were 20–50 mM potassium phosphate pH 7.4, 50 mM HEPES pH 7.5, and Universal buffer described above. Table 1 shows the various combinations of the additives used that showed the strongest signal on ELGA gels (see FIG. 1).

The lyophilized mixture consisted of three deglycerolized enzymes, trehalose to a final concentration of 6.7% (w/v), Universal Buffer to a volume of 20% (v/v), and the additives listed in Table 1. The enzymes were added in the ratio of 2 units of AMV-RT, 180 units of T7 RNA Polymerase, and 0.6 units of RNase H (25 μl NASBA® reaction format), with the total enzyme volume being about 34% of total mixture volume. The additives are listed in the final concentrations found in the stabilized enzyme mixture prior to lyophilization. BSA and sugars are added weight/volume, while buffers are added volume/volume.

TABLE 1

| Mix | Additive |
| --- | --- |
| 1 | 3 mg/ml BSA/3% maltitol/6.7% trehalose/15 mM HEPES pH 7.5 |
| 2 | 3 mg/ml BSA/3% maltitol/10% trehalose/15 mM KPi pH 7.4 |
| 3 | 3 mg/ml BSA/3% maltitol/10% trehalose/15 mM HEPES pH 7.5 |
| 4 | 3 mg/ml BSA/7.5% maltitol/6.7% trehalose/Universal buffer |
| 5 | 3 mg/ml BSA/3% maltitol/6.7% trehalose/Universal buffer |

TABLE 1-continued

| Mix | Additive |
| --- | --- |
| 6 | 3 mg/ml BSA/10.5% maltitol/6.7% trehalose/Universal buffer |
| 7 | 3 mg/ml BSA/7.5% sorbitol/6.7% trehalose/6 mM KPi pH 7.4 |

Undiluted and diluted reaction products from the 7 combinations of freeze-dried enzyme mixtures set out above are shown in lanes 1–14 in FIG. 1. Mixes 3–6 (lanes 5–12) show the strongest signal. Therefore, the additives that gave the best result were the disaccharide trehalose (6–10%) in combination with the disaccharide derivative maltitol (3–10.5%) and BSA (3 mg/ml final concentration). From these and other results, the optimal buffer was determined to be Universal buffer (see FIG. 1). This formulation was able to be incorporated into a freeze-dried mixture of enzymes that still retained their initial activity levels.

EXAMPLE 2

Figure 2:
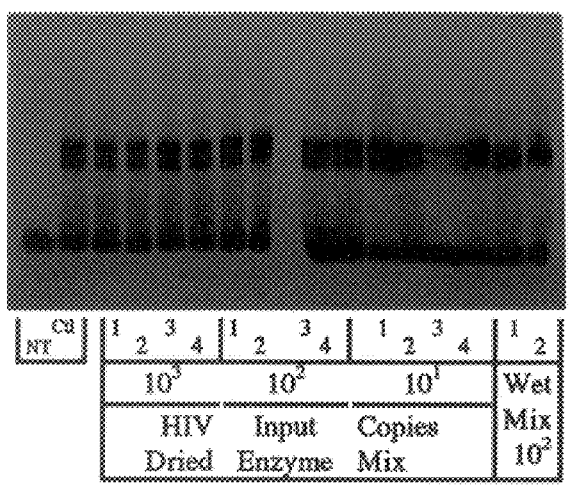
FIG. 2 is a photograph of ELGA gels, depicting the ability of a three-enzyme mix lyophilized with maltitol, BSA, dextran, and trehalose to retain multi-functional activity in the NASBA® reaction, as compared to a standard 50% glycerol wet enzyme mix.

Recovered Activity of Lyophilized NASBA® Enzyme Mix with Stabilizing Formulation A mixture of the three enzymes was made with the stabilizing formulation of BSA, maltitol, trehalose, dextran, and Universal buffer. The deglycerolized enzymes were added in the ratio of 1.6 units of AMV-RT, 144 units of T7 RNA Polymerase, and 0.48 units of RNase H per reaction (adjusted for 20 μl reaction format), with the total enzyme volume being about 15% of the total mixture volume. BSA was added to a final concentration of 3 mg/ml (w/v), maltitol to a final concentration of 10.5% (w/v), trehalose to a final concentration of 10% (w/v), Dextran T-500 to a final concentration of 2.4%, and Universal buffer to volume. The wet enzyme mixture consisted of 2 units of AMV-RT, 180 units of T7 RNA Polymerase, and 0.6 units of RNase H, along with 2.5μg BSA per reaction. The deglycerolized mixture was quick-frozen and lyophilized. After reconstitution, it showed the same ability to amplify $10^3$, $10^2$, and $10^1$ input molecules of target RNA per reaction as a wet enzyme mixture (see FIG. 2). Lane 1 is a no target (NT) or negative control. Lane 2 is a detection, or gel control, of a reaction that gave strong signal with input of $10^1$ target molecules. Lanes 3–6 are replicate reactions using $10^3$ target molecules input. Lanes 7–10 are replicate reactions using $10^2$ target molecules input. Lanes 11–14 are replicate reactions using $10^1$ target input, showing strong signal for 3 of 4 reactions. (Note that to those skilled in the art, it is expected that input of $10^1$ copies of HIV-1 RNA in NASBA® yields a 50% probability of detecting positive reaction results.) Assessment was made qualitatively, by scoring of band intensity on ELGA gels. Therefore, the ability of this enzyme mix to function in NASBA® was not impaired after lyophilization and subsequent reconstitution. As a result of these findings, all subsequent stability experiments used samples from this lyophilization run and $10^2$ input copies of HIV-1 RNA.

EXAMPLE 3

Short-term Stability Study on Lyophilized NASBA® Enzyme Mix

Figure 3:
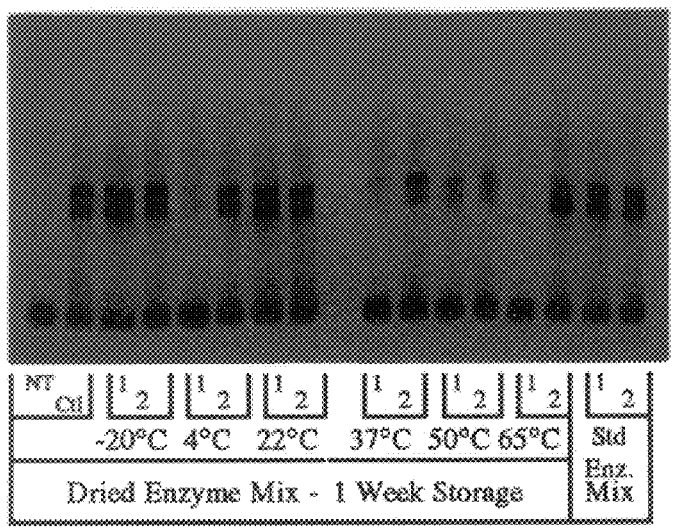
FIG. 3 is a photograph of ELGA gels, depicting the stability of a lyophilized three-enzyme mix with maltitol, BSA, dextran, and trehalose, incubated at −20° C., 4° C., 22° C., 37° C., 50° C., or 65° C. for 1 week, and tested in NASBA®.

A stability test was performed on enzyme mixtures lyophilized in the presence of BSA, maltitol, trehalose, dextran, and Universal buffer. The ratio of enzymes in the mixture was 1.6 units of AMV-RT, 144 units of T7 RNA Polymerase, and 0.48 units of RNase H, with the total enzyme volume being about 15% of the total mixture volume. BSA was added to a final concentration of 3 mg/ml (w/v), maltitol to a final concentration of 10.5% (w/v), trehalose to a final concentration of 10% (w/v), Dextran T-500 to a final concentration of 2.4%, and Universal buffer to volume. Samples were stored at six temperatures: −20° C., 4° C., 22° C., 37° C., 50° C., or 65° C. Twelve tubes containing freeze-dried spheres were placed at each of these temperatures, and samples were removed for evaluation after incubation for a 1-week period. The reference wet enzyme mixture stored at −20° C. consisted of 2 units of AMV-RT, 180 units of T7 RNA Polymerase, and 0.6 units of RNase H, along with 2.5µg BSA per reaction. Evaluation in NASBA® involved the input of $10^2$ molecules of target HIV-1 RNA per reaction. NASBA® activity was detected in samples stored at all temperatures for 1 week (see FIG. 3), although signal intensity was not reproduced in all duplicate reactions. Lane 1 shows the reaction products of a no-target (NT) control. Lane 2 is a gel control of a reaction that showed strong signal with $10^2$ target input. Lanes 3–4 are duplicates of lyophilized samples stored at −20° C., Lanes 5–6 are duplicates of lyophilized samples stored at 4° C., Lanes 7–8 are duplicates of lyophilized samples stored at 22° C., Lanes 9–10 are duplicates of lyophilized samples stored at 37° C., Lanes 11–12 are duplicates of lyophilized samples stored at 50° C., and Lanes 13–14 are duplicates of lyophilized samples stored at 65° C. Duplicate reactions using the wet enzyme mix, as shown in Lanes 15–16, are an additional positive reaction control. Control studies were also conducted which show that wet 50% glycerol enzyme mix lost all ability to amplify $10^3$ input molecules of target RNA after 1 day at 50° C., 2 days at 37° C. or after 5 days at 22° C. (data not shown).

EXAMPLE 4

Long-term Stability Studies on NASBA® Enzyme Mix

Figure 4:
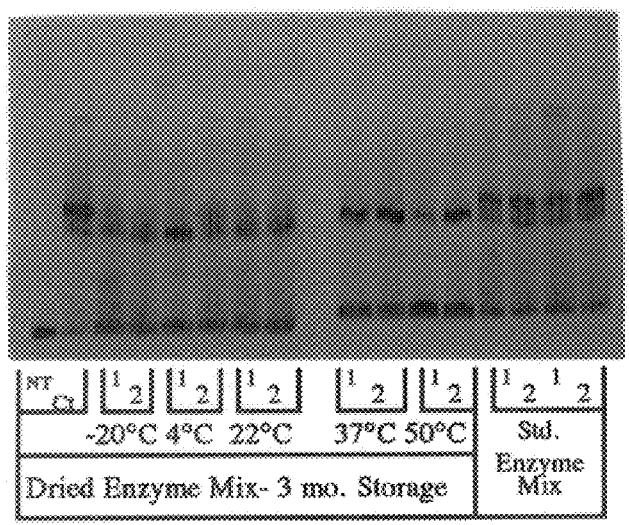
FIG. 4 is a photograph of ELGA gels, depicting the stability of a lyophilized three-enzyme mix with maltitol, BSA, dextran, and trehalose, incubated at −20° C., 4° C., 22° C., 37° C, or 50° C. for 3 months compared to a standard enzyme mix, and tested in NASBA®.

Enzyme mixtures were lyophilized in the presence of BSA, maltitol, trehalose, dextran, and Universal buffer. The deglycerolized enzymes were added in the ratio of 1.6 units of AMV-RT, 144 units of T7 RNA Polymerase, and 0.48 units of RNase H per reaction, with the total enzyme volume being about 15% of the total mixture volume. BSA was added to a final concentration of 3 mg/ml (w/v), maltitol to a final concentration of 10.5% (w/v), trehalose to a final concentration of 10% (w/v), Dextran T-500 to a final concentration of 2.4%, and Universal buffer to volume. A wet standard enzyme mix consisted of 1.6 units of AMV-RT, 144 units of T7 RNA Polymerase, and 0.48 units of RNase H per reaction. Samples were stored at five temperatures: −20° C., 4° C., 22° C., 37° C., or 50° C. (after 2 weeks storage at 65° C. there was no NASBA® signal detected). After 3 months storage, the tubes containing freeze-dried spheres were removed and reconstituted for evaluation. Evaluation in NASBA® involved the input of $10^2$ molecules of target HIV-1 RNA per reaction. NASBA® activity was detected in samples stored at all temperatures for 3 months (see FIG. 4). Lane 1 shows the reaction products of a no-target (NT) control. Lane 2 is a gel control of a reaction that showed strong signal with a target input of $10^2$ molecules. Lanes 3–4 are duplicates of lyophilized samples stored at −20° C., Lanes 5–6 are duplicates of lyophilized samples stored at 4° C., Lanes 7–8 are duplicates of lyophilized samples stored at 22° C., Lanes 9–10 are duplicates of lyophilized samples stored at 37° C., and Lanes 11–12 are duplicates of lyophilized samples stored at 50° C. Duplicate reactions using a standard enzyme mix, as shown in Lanes 13–16, are an additional positive reaction control.

Stabilizing formulations of the present invention may also be prepared as stock stabilization formulations (aqueous or dried) without enzyme so as to be used with any of a variety of enzymes, enzymatically active fragments thereof or other biological materials such as thermolabile proteins, antibodies, growth factors, cytokines, receptors, peptide hormones, and others, all of which are comprehended by the present invention.

The present invention has been described by way of illustration and with reference to specific examples and embodiments. However, this application is intended to cover those changes and substitutions which are apparent and may be made by those skilled in the art without departing from the spirit and scope of the claims. All of the references cited herein are incorporated by reference.

REFERENCES

All of the following references are incorporated herein by reference. Alonso D. O. V. and K. A. Dill. Solvent denaturation and stabilization of globular proteins. *Biochemistry*, 30: 5974–5985 (1991).

Carpenter, J. F., L. M. Crowe, and J. H. Crowe. Stabilization of phosphofructokinase with sugars during freeze-drying: characterization of enhanced protection in the presence of divalent cations. *Biochimica et Biophysica Acta*, 923: 109–115 (1987).

Compton, J. Nucleic acid sequence-based amplification. *Nature*, 350: 91–92 (1991).

Crowe, J. H., B. J. Soargo, and L. M. Crowe. Preservation of dry liposomes does not require retention of residual water. *Proc. Natl. Acad. Sci.*, 84: 1537–1540 (1987).

Davanloo, P., A. H. Rosenberg, J. J. Dunn, and F. William Studier. Cloning and expression of the gene for bacteriophage T7 RNA polymerase. *Proc. Natl. Acad. Sci.*, 81: 2035–2039 (1984).

Ford, A. W. and P. J. Dawson. The effect of carbohydrate additives in the freeze-drying of alkaline phosphatase. *J. Pharm. Pharmacol.*, 45: 86–93 (1992).

Franks, F. and R. H. M. Hatley. PAFRA, Limited. Storage of materials. U.S. Pat. No. 5,098,893. Mar. 24, 1992. (European Patent No. 0 383 569 A2).

Gianfreda, L. and M. S. Scarfi. Enzyme stabilization: state of the art. *Mol. & Cell. Biochem.*, 100: 97–128 (1991).

Guthöhrlein, G., and T. B. Helting. Behringweke Aktiengesellschaft. Stabilized polysaccharides. European Patent No. GB 2 009 198 A. Oct. 27, 1978.

Hayashi, H., and M. Komiya. A method for stabilizing tumor necrosis factor and a stable aqueous solution or powder containing the same. European Patent No. GB 2 126 588 A. Aug. 31, 1982.

Hillenbrand, G. and W. L. Staudenbauer. Discriminatory function of ribonuclease H in the selective initiation of plasmid DNA replication. *Nucleic Acids Res.*, 10: 833–853 (1982).

Houts, G. E., M. Miyagi, C. Ellis, D. Beard, and J. W. Beard. Reverse transcriptase from Avian Myeloblastosis virus. *J Virol.*, 29: 517–522 (1979).

Kievits, T., B. van Gemen, D. van Stripj, R. Schukkink, M. Dircks, H. Adriaanse, L. Malek, R. Sooknanan, P. Lens. NASBA® isothermal enzymatic in vitro nucleic acid amplification optimized for the diagnosis of HIV-1 infection. *J. Virol. Methods.*, 35: 273–286 (1991).

Malek, L. T. Cangene Corporation. Enhanced nucleic acid amplification process. U.S. Pat. No. 5,130,238. Jul. 14, 1992.

Roser, B. J. Quadrant Bioresources Limited. Protection of proteins and the like. U.S. Pat. No. 4, 891, 319. July 9, 1986. (European Patent No. WO 87/00196. Jan. 15, 1987.). Patent Application GB 2009198(A) (Behringwerk AG) discloses the lyophilisatioll of meningococcal polysaccharide and trehalose; British Patent Application GB 2126588A (Asahi Kasei KKK) discloses the stabilization of tumor necrosis factor (TNF) to lyophilisation and freezing by including either a non-ionic surfactant or trehalose (or another sugar); and Published Japanese Patent Application J 58074696A (Iatron Laboratories) discloses the freeze drying (lyophilisation) of ATP in the presence of trehalose.

Roser, B. J. Quadrant Bioresources Limited. Preservation of viruses. European Patent No. WO 89/06542. Jul. 27, 1989.

Roser, B. J. Quadrant Bioresources Limited. Method of drying macromolecules. European Patent No. WO 89/06976. Aug. 10, 1989.

Roser, B. J. Quadrant Bioresources Limited. Composition and method for stabilising organic compounds. European Patent No. EP 0 415 567 A2. Jul. 31, 1990.

Tsou, C. L. Conformational flexibility of enzyme active sites. *Science*, 262: 380–381 (1993).

van der Vliet, G. M., R. Schukkink, B. van Gemen, P. Schepers, and P. Klatser. Nucleic acid sequence-based amplification (NASBA®) for the identification of mycobacteria. *J. Gen. Micro.*, 139: 2423–2429 (1993).

What is claimed is:

1. A method for stabilizing one or more enzymes, or enzymatically active fragments thereof, for storage in the dry phase above freezing temperature, the method comprising:

(i) combining said one or more enzymes or enzymatically active fragment thereof with an aqueous stabilizing solution comprising in combination a carrier protein, from about 3% to about 15% w/v of one or more disaccharides, from about 1% to about 10% w/v of one or more disaccharide derivatives, from about 0% to about 10% w/v of one or more sugar polymers, and a compatible buffer thereby producing a mixture;

(ii) freezing the mixture obtained in step (i); and (iii) lyophilizing the frozen mixture obtained in step (ii) until substantially water-free, whereby a stabilized enzyme formulation is obtained.

2. The method of claim 1 wherein the carrier protein is bovine serum albumin.

3. The method of claim 2 wherein the concentration of bovine serum albumin is about 3 mg/ml.

4. The method of claim 1 wherein the disaccharide derivative is maltitol.

5. The method of claim 1 wherein the disaccharide is trehalose.

6. The method of claim 5 wherein trehalose is present at from about 6% to about 10% (w/v).

7. The method of claim 1 wherein the disaccharide derivative is selected from the group consisting of maltitol, mannitol, corn syrup solids, sorbitol and branched polymers of sucrose.

8. The method of claim 7 wherein the disaccharide derivative is maltitol.

9. The method of claim 8 wherein maltitol is present at from about 3% to about 10% (w/v).

10. The method of claim 1 wherein the sugar polymer is dextran.

11. The method of claim 10 wherein dextran is present at from about 2% to about 10% (w/v).

12. The method of claim 1 wherein the buffer is selected from the group consisting of Tris buffers, HEPES buffers, phosphate buffers and combinations thereof.

13. The method of claim 12 wherein the buffer consists essentially of 2.92 mM potassium phosphate pH 7.2, 4.14 mM potassium phosphate pH 7.5, 1.28 mM Tris-HCl pH 7.5, 20.7 mM NaCl, 19.2 mM KCl, 0.51 mM dithiothreitol, 0.66 mM EDTA, 1.28 mM Mg-Acetate, and 0.03% of a non-ionic surfactant.

14. A mixture for use in producing an aqueous formulation suitable for lyophilization, comprising:
(i) a carrier protein;
(ii) from about 3% to about 15% (w/v) of one or more disaccharides;
(iii) from about 1% to about 10% (w/v) of one or more disaccharide derivatives;
(iv) from about 0% to about 10% (w/v) of a sugar polymer;
(v) a compatible buffer; and
(vi) one or more enzymes.

15. The mixture of claim 14 wherein the carrier protein is bovine serum albumin.

16. The mixture of claim 15 wherein the concentration of bovine serum albumin is about 3 mg/ml.

17. The mixture of claim 14 wherein the disaccharide is selected from the group consisting of trehalose and sucrose.

18. The mixture of claim 17 wherein the disaccharide is trehalose.

19. The mixture of claim 18 wherein trehalose is present at from about 6% to about 10% (w/v).

20. The mixture of claim 14 wherein the disaccharide derivative is selected from the group consisting of maltitol, mannitol, corn syrup solids, sorbitol and branched polymers of sucrose.

21. The mixture of claim 20 wherein the disaccharide derivative is maltitol.

22. The mixture of claim 21 wherein maltitol is present at from about 3% to about 10% (w/v).

23. The mixture of claim 14 wherein the sugar polymer is dextran.

24. The mixture of claim 23 wherein dextran is present at from about 2% to about 10% (w/v).

25. The mixture of claim 14 wherein the buffer is selected from the group consisting of Tris buffers, HEPES buffers, phosphate buffers and combinations thereof.

26. The mixture of claim 25 wherein the buffer consists essentially of 2.92 mM potassium phosphate pH 7.2, 4.14 mM potassium phosphate pH 7.5, 1.28 mM Tris-HCl pH 7.5, 20.7 mM NaCl, 19.2 mM KCl, 0.51 mM dithiothreitol, 0.66 mM EDTA, 1.28 mM Mg-Acetate, and 0.03% of a non-ionic surfactant.

27. The mixture of any one of claims 14–26 further comprising an aqueous phase.

28. A stabilized mixture of one or more enzymes, or enzymatically active fragments thereof, produced by a method comprising:
(i) combining one or more enzymes, or enzymatically active fragments thereof, with an aqueous stabilizing solution comprising in combination a carrier protein, from about 1% to about 10% (w/v) of one or more disaccharide derivatives, from about 3% to about 15% (w/v) of one or more disaccharides, from about 0% to about 10% of one or more simple sugar polymers, and a compatible buffer, thereby producing a mixture;
(ii) freezing said mixture; and
(iii) lyophilizing said frozen mixture until substantially water-free, whereby a stabilized mixture of said one or more enzymes is obtained.

29. The stabilized mixture of claim 28 wherein the carrier protein is bovine serum albumin.

30. The stabilized mixture of claim 29 wherein the concentration of bovine serum albumin is about 3 mg/ml.

31. The stabilized mixture of claim 28 wherein the disaccharide is selected from the group consisting of trehalose and sucrose.

32. The stabilized mixture of claim 31 wherein the disaccharide is trehalose.

33. The stabilized mixture of claim 32 wherein trehalose is present at from about 6% to about 10% (w/v).

34. The stabilized mixture of claim 31 wherein the sugar polymer is dextran.

35. The stabilized mixture of claim 34 wherein dextran is present at from about 2% to about 10% (w/v).

36. The stabilized mixture of claim 28 wherein the disaccharide derivative is selected from the group consisting of maltitol, mannitol, corn syrup solids, sorbitol and branched polymers of sucrose.

37. The stabilized mixture of claim 36 wherein the disaccharide derivative is maltitol.

38. The stabilized mixture of claim 37 wherein maltitol is present at from about 3% to about 10% (w/v).

39. The stabilized mixture of claim 28 wherein the buffer is selected from the group consisting of Tris buffers, HEPES buffers, phosphate buffers and combinations thereof.

40. The stabilized mixture of claim 39 wherein the buffer consists essentially of 2.92 mM potassium phosphate pH 7.2, 4.14 mM potassium phosphate pH 7.5, 1.28 mM Tris-HCl pH 7.5, 20.7 mM NaCl, 19.2 mM KCl, 0.51 mM dithiothreitol, 0.66 mM EDTA, 1.28 mM Mg-Acetate, and 0.03% of a non-ionic surfactant.

41. An aqueous enzyme formulation useful for stabilizing one or more enzymes, or enzymatically active fragments thereof, produced by a method comprising combining with an aqueous phase:
(i) a carrier protein;
(ii) from about 1% to about 10% (w/v) of one or more disaccharide derivatives;
(iii) from about 3% to about 15% (w/v) of one or more disaccharides;
(iv) from about 0% to about 10% of one or more simple sugar polymers;
(v) a compatible buffer; and
(vi) one or more enzymes, or enzymatically active fragments thereof.

42. The formulation of claim 41 wherein the carrier protein is bovine serum albumin.

43. The formulation of claim 42 wherein the concentration of bovine serum albumin is about 3 mg/ml.

44. The formulation of claim 41 wherein the disaccharide is selected from the group consisting of trehalose and sucrose.

45. The formulation of claim 44 wherein the disaccharide is trehalose.

46. The formulation of claim 45 wherein trehalose is present at from about 6% to about 10% (w/v).

47. The formulation of claim 44 wherein the disaccharide derivative is maltitol.

48. The formulation of claim 47 wherein maltitol is present at from about 3% to about 10% (w/v).

49. The formulation of claim 41 wherein the sugar polymer is dextran.

50. The formulation of claim 49 wherein dextran is present at from about 2% to about 10% (w/v).

51. The formulation of claim 41 wherein the buffer is selected from the group consisting of Tris buffers, HEPES buffers, phosphate buffers and combinations thereof.

52. The formulation of claim 51 wherein the buffer consists essentially of 2.92 mM potassium phosphate pH 7.2, 4.14 mM potassium phosphate pH 7.5, 1.28 mM Tris-HCl pH 7.5, 20.7 mM NaCl, 19.2 mM KCl, 0.51 mM dithiothreitol, 0.66 mM EDTA, 1.28 mM Mg-Acetate, and 0.03% of a non-ionic surfactant.

53. The aqueous formulation of claim 41 wherein the disaccharide derivative is selected from the group consisting of maltitol, mannitol, corn syrup solids, sorbitol and branched polymers of sucrose.

54. A stabilized, substantially water-free mixture of one or more enzymes or enzymatically active fragments thereof comprising:
- (i) a carrier protein;
- (ii) from about 3% to about 15% (w/v) of one or more disaccharides;
- (iii) from about 1% to about 10% (w/v) of one or more disaccharide derivatives;
- (iv) from 0% to about 10% (w/v) of a sugar polymer;
- (v) a compatible buffer; and
- (vi) one or more enzymes.

55. The stabilized mixture of claim 54 wherein the carrier protein is bovine serum albumin.

56. The stabilized mixture of claim 55 wherein the concentration of bovine serum albumin is about 3 mg/ml.

57. The stabilized mixture of claim 54 wherein the disaccharide is selected from the group consisting of trehalose and sucrose.

58. The stabilized mixture of claim 57 wherein the disaccharide is trehalose.

59. The stabilized mixture of claim 58 wherein trehalose is present at from about 6% to about 10% (w/v).

60. The stabilized mixture of claim 57 wherein the sugar polymer is dextran.

61. The stabilized mixture of claim 60 wherein dextran is present at from about 2% to about 10% (w/v).

62. The stabilized mixture of claim 54 wherein the disaccharide derivative is selected from the group consisting of maltitol, mannitol, corn syrup solids, sorbitol and branched polymers of sucrose.

63. The stabilized mixture of claim 62 wherein the disaccharide derivative is maltitol.

64. The stabilized mixture of claim 63 wherein maltitol is present at from about 3% to about 10% (w/v).

65. The stabilized mixture of claim 54 wherein the compatible buffer comprises a buffer selected from the group consisting of Tris buffers, HEPES buffers, phosphate buffers and combinations thereof.

66. The stabilized mixture of claim 65 wherein the compatible buffer consists essentially of 2.92 mM potassium phosphate pH 7.2, 4.14 mM potassium phosphate pH 7.5, 1.28 mM Tris-HCl pH 7.5, 20.7 mM NaCl, 19.2 mM KCl, 0.51 mM dithiothreitol, 0.66mM EDTA, 1.28 mM Mg-Acetate, and 0.03% of a non-ionic surfactant.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

AGTGGGGGGA CATCAAGCAG CCATGCAAA    29

(2) INFORMATION FOR SEQ ID NO:2:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

AATTCTAATA CGACTCACTA TAGGGTGCTA TGTCACTTCC CCTTGGTTCT CTCA    54